United States Patent
Zhi et al.

(10) Patent No.: US 7,084,151 B2
(45) Date of Patent: Aug. 1, 2006

(54) 5-(1',1'-CYCLOALKYL/ALKENYL)METHYLIDENE 1,2-DIHYDRO-5H-CHROMENO[3,4-f]QUINOLINES AS SELECTIVE PROGESTERONE RECEPTOR MODULATOR COMPOUNDS

(75) Inventors: Lin Zhi, San Diego, CA (US); Cornelis Arjan Van Oeveren, Carlsbad, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 10/684,227

(22) Filed: Oct. 10, 2003

(65) Prior Publication Data

US 2004/0147530 A1   Jul. 29, 2004

Related U.S. Application Data

(60) Provisional application No. 60/418,140, filed on Oct. 11, 2002.

(51) Int. Cl.
*A61K 31/4741* (2006.01)
*C07D 491/02* (2006.01)

(52) U.S. Cl. ............ 514/285; 546/62; 544/55; 544/96; 544/333; 514/226.8; 514/228.8; 514/256

(58) Field of Classification Search .......... 514/285, 514/226.8, 228.8, 256; 546/62; 544/55, 544/96, 333
See application file for complete search history.

(56) References Cited

U.S. PATENT DOCUMENTS

| | | | |
|---|---|---|---|
| 5,506,102 A | 4/1996 | McDonnell et al. | 435/6 |
| 5,688,808 A | 11/1997 | Jones et al. | 514/285 |
| 5,688,810 A | 11/1997 | Jones et al. | 514/311 |
| 5,693,646 A | 12/1997 | Jones et al. | |
| 5,693,647 A | 12/1997 | Jones et al. | |
| 5,696,127 A | 12/1997 | Jones et al. | |
| 5,696,130 A | 12/1997 | Jones et al. | 514/291 |
| 5,696,133 A | 12/1997 | Jones et al. | 514/314 |
| 5,808,139 A | 9/1998 | Pathirana et al. | 560/138 |
| 5,994,544 A | 11/1999 | Jones et al. | 546/62 |
| 6,001,846 A | 12/1999 | Bender et al. | 514/285 |
| 6,093,821 A | 7/2000 | Jones et al. | 544/333 |
| 6,093,825 A | 7/2000 | Bender et al. | 546/62 |
| 6,093,826 A | 7/2000 | Edwards et al. | 546/62 |
| 6,121,450 A | 9/2000 | Jones et al. | 546/81 |
| 6,172,241 B1 | 1/2001 | Edwards et al. | 549/280 |
| 6,268,497 B1 | 7/2001 | Edwards et al. | 546/62 |
| 6,306,851 B1 | 10/2001 | Santilli et al. | 514/230.5 |
| 6,319,912 B1 | 11/2001 | Grubb et al. | 514/171 |
| 6,329,416 B1 | 12/2001 | Grubb et al. | 514/415 |
| 6,339,098 B1 | 1/2002 | Collins et al. | 514/373 |
| 6,355,648 B1 | 3/2002 | Fensome et al. | 514/275 |
| 6,358,947 B1 | 3/2002 | Zhi et al. | 514/229.5 |
| 6,358,948 B1 | 3/2002 | Zhang et al. | 514/230.5 |
| 6,369,056 B1 | 4/2002 | Zhang et al. | 514/230.5 |
| 6,380,178 B1 | 4/2002 | Grubb et al. | 514/171 |
| 6,380,207 B1 | 4/2002 | Coghlan et al. | 514/285 |
| 6,380,235 B1 | 4/2002 | Zhang et al. | 514/395 |
| 6,391,907 B1 | 5/2002 | Fensome et al. | 514/409 |
| 6,399,593 B1 | 6/2002 | Grubb et al. | 514/171 |
| 6,407,101 B1 | 6/2002 | Collins et al. | 514/230.5 |
| 6,417,214 B1 | 7/2002 | Ullrich et al. | 514/378 |
| 6,436,929 B1 | 8/2002 | Zhang et al. | 514/230.5 |
| 6,441,019 B1 | 8/2002 | Santilli et al. | 514/409 |
| 6,444,668 B1 | 9/2002 | Grubb et al. | 514/230.5 |
| 6,448,405 B1 | 9/2002 | Jones et al. | 546/62 |
| 6,462,032 B1 | 10/2002 | Grubb et al. | 514/171 |
| 6,498,154 B1 | 12/2002 | Grubb et al. | 514/171 |
| 6,503,939 B1 | 1/2003 | Grubb et al. | 514/415 |
| 6,506,766 B1 | 1/2003 | Coghlan et al. | 514/285 |
| 6,509,334 B1 | 1/2003 | Zhang et al. | 514/230.5 |
| 6,521,657 B1 | 2/2003 | Fensome et al. | 514/414 |
| 6,544,970 B1 | 4/2003 | Grubb et al. | 514/171 |
| 6,566,358 B1 | 5/2003 | Zhang et al. | 514/230.5 |
| 6,566,372 B1 | 5/2003 | Zhi et al. | 514/312 |
| 6,583,145 B1 | 6/2003 | Fensome et al. | 514/256 |
| 6,608,068 B1 | 8/2003 | Fensome et al. | 514/256 |
| 6,693,103 B1 | 2/2004 | Zhang et al. | 514/256 |
| 6,696,459 B1 | 2/2004 | Jones et al. | 514/285 |
| 6,713,478 B1 | 3/2004 | Zhang et al. | 514/230.5 |
| 6,759,408 B1 | 7/2004 | Grubb et al. | 514/230.5 |
| 6,794,373 B1 | 9/2004 | Grubb et al. | 514/171 |
| 6,835,744 B1 | 12/2004 | Ullrich et al. | 514/409 |
| 6,841,568 B1 | 1/2005 | Fensome et al. | 514/415 |
| 2003/0216388 A1 | 11/2003 | Zhang et al. | 514/230.5 |
| 2003/0220388 A1 | 11/2003 | Fensome et al. | 514/414 |
| 2003/0225109 A1 | 12/2003 | Fensome et al. | 514/256 |
| 2004/0152717 A1 | 8/2004 | Zhi et al. | 514/285 |
| 2004/0152718 A1 | 8/2004 | Zhi et al. | 514/285 |

(Continued)

FOREIGN PATENT DOCUMENTS

WO   WO 96/19458   6/1996

(Continued)

OTHER PUBLICATIONS

Berger, T.S., et al., J. Steroid Biochem. Mol. Bio. 1992, 41, 733–738.

(Continued)

*Primary Examiner*—Charanjit S. Aulakh
(74) *Attorney, Agent, or Firm*—Fish & Richardson P.C.; Stephanie Seidman; Frank J. Miskiel

(57) ABSTRACT

The present invention is directed to compounds, pharmaceutical compositions, and methods for modulating processes mediated by Progesterone Receptor. Also provided are methods of making such compounds and pharmaceutical compositions.

11 Claims, No Drawings

U.S. PATENT DOCUMENTS

| | | | |
|---|---|---|---|
| 2004/0186101 A1 | 9/2004 | Zhang et al. | 514/230.5 |

FOREIGN PATENT DOCUMENTS

| | | |
|---|---|---|
| WO | WO 99/41256 A1 | 8/1999 |
| WO | 0066103 | 11/2000 |
| WO | 0066163 | 11/2000 |
| WO | 0066164 | 11/2000 |
| WO | 0066165 | 11/2000 |
| WO | 0066166 | 11/2000 |
| WO | 0066167 | 11/2000 |
| WO | 0066168 | 11/2000 |
| WO | 0066225 | 11/2000 |
| WO | 0066554 | 11/2000 |
| WO | 0066555 | 11/2000 |
| WO | 0066556 | 11/2000 |
| WO | 0066560 | 11/2000 |
| WO | 0066564 | 11/2000 |
| WO | 0066570 | 11/2000 |
| WO | 0066571 | 11/2000 |
| WO | 0066574 | 11/2000 |
| WO | 0066581 | 11/2000 |
| WO | 0066590 | 11/2000 |
| WO | 0066591 | 11/2000 |
| WO | 0066592 | 11/2000 |
| WO | 0116108 | 3/2001 |
| WO | WO 02/02565 | 1/2002 |
| WO | WO 99/41257 A1 | 4/2002 |
| WO | 2004033459 | 4/2004 |
| WO | 2004033460 | 4/2004 |
| WO | 2004033461 | 4/2004 |

OTHER PUBLICATIONS

Pathirana, C., et al., Mol. Pharm. 1995, 47, 630-635.

International Search Report for related PCT International Application No. PCT/US03/24416 filed Apr. 8, 2003.

Tegley, C.M. et al., "5-Benzylidene 1,2-Dihydrochromemo[3,4-*f*]quinolines, A Novel Class of Nonsteroidal Human Progesterone Receptor Agonists" J. Med. Chem. 1998, 41, 4354-4359.

Zhi, L. et al., "Synthesis and Biological Activity of 5-Methylidene 1,2-Dihydrochromeno[3-4-*f*]quinoline Derivatives as Progesterone Receptor Modulators." *Bioorganic & Medicinal Chemistry Letters* 13(2003) 2071-2074.

Clemm et al., "Definition of the critical cellular components which distinguish between hormone and antihormone activated progesterone receptor," Journal of Steroid Biochemistry and Molecular Biology 53(1-6):487-495. (1995).

Crombie et al., "Anti-progesterone effects on maternal recognition and behavior imprinted during first pregnancy in mice," Journal of Endocrinology 147(2):331-337. (1995).

Edwards et al., "5-Aryl-1,2-dihydro-5H-chromeno[3,4-*f*]quinolines as potent, orally active, nonsteroidal progesterone receptor agonists: the effect of D-ring substituents," Journal of Medicinal Chemistry. 41(3):303-310 (1998).

Edwards et al., "Preparation, resolution, and biological evaluation of 5-aryl-1, 2-dihydro-5H-chromeno[3,4-f]quinolines: potent, orally active, nonsteroidal progesterone receptor agonists," Journal of Medicinal Chemistry 41(15):2779-2785 (1998).

Hamann et al., "Nonsteroidal progesterone receptor antagonists based on a conformationally-restricted subseries of 6-aryl-1,2-dihydro-2,2,4-trimethylquinolines," Bioorganic & Medicinal Chemistry Letters 8(19):2731-2736 (1998).

Mais et al., "Specific interactions of progestins and anti-progestins with progesterone antibodies, plasma binding proteins and the human recombinant receptor," Journal of Steroid Biochemistry and Molecular Biology 54(1-2):63-69. (1995).

McDonnell, D.P. and M.E. Goldman, "RU486 exerts antiestrogenic activities through a novel progesterone receptor A form-mediated mechanism," The Journal of Biological Chemistry 269(16):11945-11949. (1994).

McDonnell et al., "Definition of the cellular mechanisms which distinguish between hormone and antihormone activated steroid receptors," Seminars in Cancer Biology, 5(5):327-336 (1994).

McDonnell et al., "The human progesterone receptor A-form functions as a transcriptional modulator of mineralocorticoid receptor transcriptional activity," Journal of Steroid Biochemistry and Molecular Biology 48(5-6):425-432. (1994).

Miner, J.N. and C.M. Tyree, "Drug discovery and the intracellular receptor family," Vitamins and Hormones. 62:253-280. (2001).

Parandoosh et al., "Progesterone and oestrogen receptors in the decidualized mouse uterus and effects of different types of anti-progesterone treatment," Journal of Reproduction and Fertility 105(2):215-220. (1995).

Rosen et al., "Intracellular receptors and signal transducers and activators of transcription superfamilies—novel targets for small-molecule drug discovery," Journal of Medicinal Chemistry 38(25):4855-4874 (1995).

Santiso-Mere, D. and D.P. McDonnell, "Applied nuclear receptor research in the drug discovery process," Chimica Oggi 12(5-6):29-36. (1994).

Taylor et al., "Activity of progesterone and anti-progestins in a rat mammary primary cell culture system," Journal of Steroid Biochemistry and Molecular Biology 58(1):117-121 (1996).

Vegeto et al., "Human progesterone receptor A form is a cell- and promoter-specific repressor of human progesterone receptor B function," Molecular Endocrinology. 7(10):1244-1255. (1993).

Wagner et al., "The novel progesterone receptor antagonists RTI 3021-012 and RTI 3021-022 exhibit complex glucocorticoid receptor antagonist activities: Implications for the development of dissociated antiprogestins," Endocrinology 140(3):1449-1458 (1999).

Wen et al., "The A and B isoforms of the human progesterone receptor operate through distinct signaling pathways within target cells," Molecular and Cellular Biology 14(12):8356-8364 (1994).

Zhang et al., "6-Aryl-1,4-dihydro-benzo[d][1,3]oxazin-2-ones: A Novel Class of Potent, Selective, and Orally Active Nonsteroidal Progesterone Receptor Antagonists," Journal of Medicinal Chemistry 45(20):4379-4382 (2002).

Zhang et al., "Synthesis and progesterone receptor antagonist activities of 6-aryl benzimidazolones and benzothiazolones," Bioorganic & Medicinal Chemistry Letters 11(20):2747-2750 (2001).

Zhi, L. and K.B. Marschke, "Novel class of non-steroidal progesterone receptor antagonists," Expert Opinion on Therapeutic Patents. 9(6):695-700 (1999).

Zhi et al., "Development of progesterone receptor antagonists from 1,2-dihydrochromeno[3,4-*f*]quinoline agonist pharmacophore," Bioorganic & Medicinal Chemistry Letters. 13(12):2075-2078. (2003).

Zhi et al., "5-Alkyl 1,2-dihydrochromeno[3,4-*f*]quinolines: a novel class of nonsteroidal progesterone receptor modulators," Bioorganic & Medicinal Chemistry Letters 8(23):3365-3370 (1998).

Zhi et al., "5-Aryl-1,2-dihydrochromeno[3,4-*f*]quinolines: a novel class of nonsteroidal human progesterone receptor agonists," Journal of Medicinal Chemistry 41(3):291-302 (1998).

Zhi et al., "5-Aryl-1,2,3,4-tetrahydrochromeno[3,4-*f*]quinolin-3-ones as a novel class of nonsteroidal progesterone receptor agonists: effect of A-ring modification," Journal of Medicinal Chemistry. 42(8):1466-1472 (1999).

Zhi et al., "5-Benzylidene-1,2-dihydrochromeno[3,4-*f*]quinolines as Selective Progesterone Receptor Modulators," Journal of Medicinal Chemistry 46(19):4104-4112 (2003).

Zhi et al., "Nonsteroidal progesterone receptor antagonists based on 6-thiophenehydroquinolines," Bioorganic & Medicinal Chemistry Letters. 10(5):415-418 (2000).

5-(1',1'-CYCLOALKYL/ALKENYL)METHYLIDENE 1,2-DIHYDRO-5H-CHROMENO[3,4-f]QUINOLINES AS SELECTIVE PROGESTERONE RECEPTOR MODULATOR COMPOUNDS

RELATED APPLICATIONS

This application claims the benefit of priority of U.S. Provisional Application Ser. No. 60/418,140 filed Oct. 11, 2002, the entire disclosure of which is incorporated herein by reference.

FIELD OF THE INVENTION

This invention relates to nonsteroidal 5-(1',1'-cycloalkyl/alkenyl)methylidene 1,2-dihydro-5H-chromeno[3,4-f]quinolines that may be modulators (i.e., agonists, partial agonists and antagonists) of progesterone receptors and to methods for the making and use of such compounds.

BACKGROUND OF THE INVENTION

Progesterone receptor (PR) modulators have been widely used in regulation of female reproduction systems and in treatment of female hormone dependent diseases. The effectiveness of known steroidal PR modulators is often tempered by their undesired side-effect profile, particularly during long-term administration. For example, the effectiveness of synthetic progestins, such as norgestrel, as female birth control agents must be weighed against the increased risk of breast cancer and heart disease. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a glucocorticoid receptor (GR) antagonist. Accordingly, identification of compounds that have good receptor-selectivity for PR over other steroid hormone receptors as well as good tissue-selectivity (e.g., selectivity for uterine tissue over breast tissue) would be of significant value in the improvement of women's health.

A group of nonsteroidal molecules, which contain a di- or tetra-hydroquinoline ring as core pharmacophore (U.S. Pat. Nos. 5,693,646; 5,693,647 and 5,696,127; PCT Int. Pub. Nos. WO 99/41256 A1 and WO 99/41257 A1) have been described as steroid receptor modulator compounds.

The entire disclosures of the patents, publications and references referred to herein are incorporated by reference herein and are not admitted to be prior art.

SUMMARY OF THE INVENTION

The present invention is directed to compounds, pharmaceutical compositions, and methods for modulating processes mediated by Progesterone Receptor. More particularly, the invention relates to nonsteroidal compounds and compositions which may be high affinity, high specificity agonists, partial agonists (i.e., partial activators and/or tissue-specific activators) and/or antagonists for progesterone receptors. Also provided are methods of making such compounds and pharmaceutical compositions.

Compounds of the present invention may be represented by the formulae:

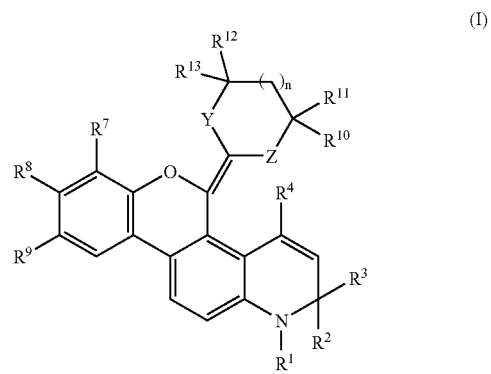

(I)

wherein:
$R^1$ is selected from the group of hydrogen, $C_1$–$C_4$ alkyl, $C_1$–$C_4$ haloalkyl, $C_1$–$C_4$ heteroalkyl, $COR^5$, $CO_2R^5$, $SO_2R^5$, and $CONR^5R^6$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ is selected from the group of hydrogen, F, Cl, Br, CN, $OR^5$, $C_1$–$C_4$ alkyl, $C_1$–$C_4$ haloalkyl, and $C_1$–$C_4$ heteroalkyl;

$R^5$ and $R^6$ each is independently selected from the group of hydrogen, $C_1$–$C_4$ alkyl, $C_1$–$C_4$ heteroalkyl, and $C_1$–$C_4$ haloalkyl;

$R^7$ through $R^9$ each independently is selected from the group of hydrogen, F, Cl, Br, I, $NO_2$, CN, $OR^5$, $NR^5R^6$, $SR^5$, $COR^5$, $CO_2R^5$, $CONR^5R^6$, $C_1$–$C_8$ alkyl, $C_1$–$C_8$ heteroalkyl, $C_1$–$C_8$ haloalkyl, $C_2$–$C_8$ alkenyl, $C_2$–$C_8$ alkynyl;

$R^{10}$ through $R^{15}$ each independently is selected from the group of hydrogen, F, Cl, Br, $OR^5$, $C_1$–$C_4$ alkyl, $C_1$–$C_4$ haloalkyl, and $C_1$–$C_4$ heteroalkyl; or $R^{12}$ and $R^{14}$ taken together form a bond, when Y is $CR^{14}R^{15}$; or $R^{10}$ and $R^{14}$ taken together form a bond, when Z is $CR^{14}R^{15}$;

Y and Z each independently is selected from the group of O, S, $NR^6$ and $CR^{14}R^{15}$;

n is 0, 1, 2, or 3;

and pharmaceutically acceptable salts and prodrugs thereof.

DEFINITIONS AND NOMENCLATURE

As used herein, the following terms are defined with the following meanings, unless explicitly stated otherwise. Furthermore, in an effort to maintain consistency in the naming of compounds of similar structure but differing substituents, the compounds described herein are named according to the following general guidelines. The numbering system for the location of substituents on such compounds is also provided.

A 5H-chromeno[3,4-f]quinoline is defined by the following structure:

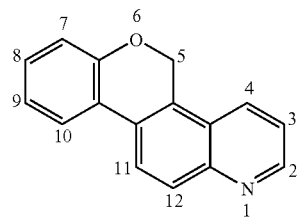

The term "alkyl," alone or in combination, refers to an optionally substituted straight-chain or branched-chain or cyclic-chain alkyl radical having from 1 to about 12 carbon atoms. The term also includes substituted straight-chain or branched-chain alkyl radicals having from 1 to about 6 carbon atoms as well as those having from 1 to about 4 carbon atoms. Examples of alkyl radicals include methyl, ethyl, n-propyl, isopropyl, cyclopropyl, n-butyl, isobutyl, sec-butyl, tert-butyl, tert-amyl, pentyl, hexyl, heptyl, octyl and the like.

The term "alkenyl," alone or in combination, refers to an optionally substituted straight-chain or branched-chain hydrocarbon radical having one or more carbon-carbon double-bonds and having from 2 to about 18 carbon atoms. The term also includes substituted straight-chain or branched-chain alkyl radicals having one or more carbon-carbon double bonds and having from 2 to about 6 carbon atoms as well as those having from 2 to about 4 carbon atoms. Examples of alkenyl radicals include ethenyl, propenyl, 1,3-butadienyl and the like.

The term "alkynyl," alone or in combination, refers to an optionally substituted straight-chain or branched-chain hydrocarbon radical having one or more carbon-carbon triple-bonds and having from 2 to about 12 carbon atoms. The term also includes substituted straight-chain or branched-chain alkyl radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The term "heteroalkyl," "heteroalkenyl" and "heteroalkynyl" refer to alkyl, alkenyl and alkynyl radicals, respectively, as described above, in which one or more skeletal atoms are heteroatoms such as, for example, oxygen, nitrogen, sulfur or combinations thereof. The terms heteroalkyl, heteroalkenyl and heteroalkynyl include radicals in which 1 to about 6 skeletal atoms are oxygen, nitrogen, sulfur or combinations thereof, as well as those in which 1 to 4 skeletal atoms are oxygen, nitrogen, sulfur or combinations thereof and those in which 1 to 2 skeletal atoms are oxygen, nitrogen, sulfur or combinations thereof.

The terms haloalkyl, haloalkenyl, haloalkynyl and haloalkoxy include alkyl, alkenyl, and alkynyl structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl radicals.

The term "halogen" includes F, Cl, Br and I.

The term "mediate" means affect or influence, frequently indirectly or via some intervening action. Thus, for example, conditions mediated by a progesterone receptor are those in which a progesterone receptor plays a role. Progesterone receptors are known to play a role in conditions including, for example, infertility, contraception, pregnancy maintenance and termination, female hormone deficiency, female sexual dysfunction, dysfunctional uterine bleeding, endometriosis, mood disorder, osteoporosis, and hormone-dependent cancers.

The term "receptor-selectivity" refers to the conditions where a compound displays modulating activity towards one or more particular receptors (e.g., a progesterone receptors) while displaying substantially less or no cross-reactivity towards one or more different receptors (e.g., glucocorticoid receptors). Thus, for example, selective compounds of the present invention may display modulating activity towards progesterone receptors without displaying substantial cross-reactivity towards another steroid hormone receptors. Compounds may be selective for a single receptor, group of similar receptors or multiple receptors.

The term "tissue-selectivity" refers to compounds that display substantial modulating activity in one tissue (e.g., uterine tissue) while displaying lesser modulating activity in at least one other tissue (e.g., breast tissue). Thus, for example, tissue-selective compounds of the present invention may display substantial modulating activity in uterine and vaginal tissues with lesser modulating activity (partial agonistic or partial antagonistic) in breast tissues relative to the activities of the marketed steroidal progestins in all of the target tissues.

The term "modulate" means affect or influence, for example, the amount, degree or proportion. Thus, compounds that "modulate" a receptor affect the activity, either positively or negatively, of that receptor. The term may be used to refer to the activity of compounds of a receptor as, for example, an agonist, partial agonist or antagonist. The term also may be used to refer to the effect that a compound has on a physical and/or physiological condition of an individual. For example, certain compounds of the present invention may be used to modulate fertility in an individual. That is, certain compounds of this invention may be used to increase the fertility of an individual, while other compounds of this invention may be used to decrease the fertility of an individual.

A compound that binds to a receptor and mimics the effect of the native or endogenous ligand is referred to as an "agonist," while a compound that binds to a receptor and inhibits or has an effect that is opposite that of the native or endogenous ligand is called an "antagonist." "Partial agonists" give an effect of the same type as the native or endogenous ligand, but of a lower magnitude, while "partial antagonists" are incompletely inhibitory or opposite that of the native or endogenous ligand.

DETAILED DESCRIPTION OF THE INVENTION

Compounds of the present invention may be represented by the formulae:

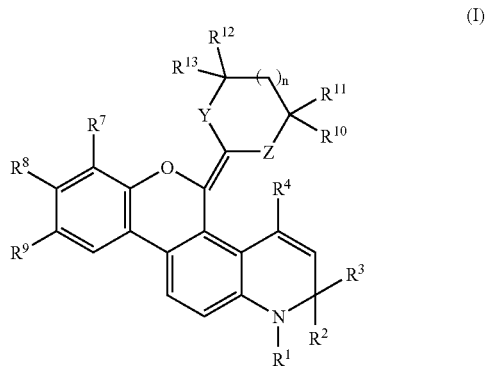

(I)

wherein:

$R^1$ is selected from the group of hydrogen, $C_1$–$C_4$ alkyl, $C_1$–$C_4$ haloalkyl, $C_1$–$C_4$ heteroalkyl, $COR^5$, $CO_2R^5$, $SO_2R^5$, and $CONR^5R^6$;

$R^2$ and $R^3$ each independently is selected from the group of hydrogen, $C_1$–$C_6$ alkyl, and $C_1$–$C_6$ haloalkyl; or $R^2$ and $R^3$ taken together form a cycloalkyl ring of from three to twelve carbons;

$R^4$ is selected from the group of hydrogen, F, Cl, Br, CN, $OR^5$, $C_1$–$C_4$ alkyl, $C_1$–$C_4$ haloalkyl, and $C_1$–$C_4$ heteroalkyl;

$R^5$ and $R^6$ each is independently selected from the group of hydrogen, $C_1$–$C_4$ alkyl, $C_1$–$C_4$ heteroalkyl, and $C_1$–$C_4$ haloalkyl;

$R^7$ through $R^9$ each independently is selected from the group of hydrogen, F, Cl, Br, I, $NO_2$, CN, $OR^5$, $NR^5R^6$, $SR^5$, $COR^5$, $CO_2R^5$, $CONR^5R^6$, $C_1$–$C_8$ alkyl, $C_1$–$C_8$ heteroalkyl, $C_1$–$C_8$ haloalkyl, $C_2$–$C_8$ alkenyl, $C_2$–$C_8$ alkynyl;

$R^{10}$ through $R^{15}$ each independently is selected from the group of hydrogen, F, Cl, Br, $OR^5$, $C_1$–$C_4$ alkyl, $C_1$–$C_4$ haloalkyl, and $C_1$–$C_4$ heteroalkyl; or $R^{12}$ and $R^{14}$ taken together form a bond, when Y is $CR^{14}R^{15}$; or $R^{10}$ and $R^{14}$ taken together form a bond, when Z is $CR^{14}R^{15}$;

Y and Z each independently is selected from the group of O, S, $NR^6$ and $CR^{14}R^{15}$;

n is 0, 1, 2, or 3;

and pharmaceutically acceptable salts and prodrugs thereof.

Compounds of the invention include those represented by the formulae:

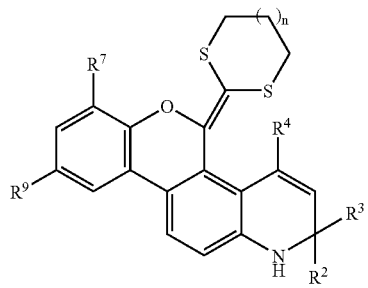

(II)

wherein:

$R^2$ and $R^3$ each independently is selected from the group of $C_1$–$C_4$ alkyl, and $C_1$–$C_4$ haloalkyl;

$R^4$ is selected from the group of hydrogen, F, Cl, Br, CN, $OR^5$, $C_1$–$C_4$ alkyl, $C_1$–$C_4$ haloalkyl, and $C_1$–$C_4$ heteroalkyl;

$R^5$ and $R^6$ each is independently selected from the group of hydrogen, $C_1$–$C_4$ alkyl, $C_1$–$C_4$ heteroalkyl, and $C_1$–$C_4$ haloalkyl;

$R^7$ through $R^9$ each independently is selected from the group of hydrogen, F, Cl, Br, CN, $OR^5$, $NR^5R^6$, $SR^5$, $COR^5$, $C_1$–$C_4$ alkyl, $C_1$–$C_4$ heteroalkyl, $C_1$–$C_4$ haloalkyl, $C_2$–$C_4$ alkenyl;

n is 0, 1, 2, or 3;

and pharmaceutically acceptable salts and prodrugs thereof.

In the following table, the inventors contemplate any combination of the following Markush groups and those described above for the various variables.

TABLE A

Table of Markush Groups by Variable

| | Markush Group A | Markush Group B | Markush Group C | Markush Group D |
|---|---|---|---|---|
| $R_1$ | H, $C_1$—$C_4$ alkyl, $C_1$—$C_4$ haloalkyl, $C_1$—$C_4$ heteroalkyl, $COR^5$, $CO_2R^5$, $SO_2R^5$ and $CONR^5R^6$ | H, $C_1$—$C_4$ alkyl, $COR^5$, $CO_2R^5$ and $SO_2R^5$ | methyl and H | H |
| $R_2$ | H, $C_1$—$C_6$ alkyl and $C_1$—$C_6$ haloalkyl $R^2$ and $R^3$ taken together form a $C_3$—$C_{12}$ cycloalkyl ring | $C_1$—$C_4$ alkyl, and $C_1$—$C_4$ haloalkyl $R^2$ and $R^3$ taken together form a $C_4$—$C_8$ cycloalkyl ring | $C_1$—$C_4$ alkyl $R^2$ and $R^3$ taken together form a $C_5$—$C_6$ cycloalkyl ring | $CH_3$ |
| $R_3$ | H, $C_1$—$C_6$ alkyl and $C_1$—$C_6$ haloalkyl $R^2$ and $R^3$ taken together form a $C_3$—$C_{12}$ cycloalkyl ring | $C_1$—$C_4$ alkyl and $C_1$—$C_4$ haloalkyl $R^2$ and $R^3$ taken together form a $C_4$—$C_8$ cycloalkyl ring | $C_1$—$C_4$ alkyl $R^2$ and $R^3$ taken together form a $C_5$—$C_6$ cycloalkyl ring | $CH_3$ |
| $R_4$ | H, F, Cl, Br, CN, $OR^5$, $C_1$—$C_4$ alkyl, $C_1$—$C_4$ haloalkyl and $C_1$—$C_4$ heteroalkyl | H, F, Cl, Br, $C_1$—$C_4$ alkyl and $C_1$—$C_4$ haloalkyl | F, Cl, Br, $CH_3$ and $CF_3$ | methyl |
| $R_5$ | H, $C_1$—$C_4$ alkyl, $C_1$—$C_4$ heteroalkyl and $C_1$—$C_4$ haloalkyl | H and $C_1$—$C_4$ alkyl | H and methyl | H |
| $R_6$ | H, $C_1$—$C_4$ alkyl, $C_1$—$C_4$ heteroalkyl and $C_1$—$C_4$ haloalkyl | H, and $C_1$—$C_4$ alkyl | H and methyl | H |
| $R_7$ | H, F, Cl, Br, I, $NO_2$, CN, $OR^5$, $NR^5R^6$, $SR^5$, $COR^5$, $CO_2R^5$, $CONR^5R^6$, $C_1$—$C_8$ alkyl, $C_1$—$C_8$ heteroalkyl, $C_1$—$C_8$ haloalkyl, $C_2$—$C_8$ | H, F, Cl, Br, CN, $OR^5$, $NR^5R^6$, $SR^5$, $COR^5$, $C_1$—$C_4$ alkyl, $C_1$—$C_4$ heteroalkyl, $C_1$—$C_4$ haloalkyl and $C_2$—$C_4$ alkenyl | hydrogen, F, Cl, Br, CN, $OR^5$, $C_1$—$C_8$ alkyl, $C_1$—$C_8$ heteroalkyl and $C_1$—$C_8$ haloalkyl | H or F |

TABLE A-continued

Table of Markush Groups by Variable

| | Markush Group A | Markush Group B | Markush Group C | Markush Group D |
|---|---|---|---|---|
| | alkenyl and $C_2$—$C_8$ alkynyl | | | |
| $R_8$ | H, F, Cl, Br, I, $NO_2$, CN, $OR^5$, $NR^5R^6$, $SR^5$, $COR^5$, $CO_2R^5$, $CONR^5R^6$, $C_1$—$C_8$ alkyl, $C_1$—$C_8$ heteroalkyl, $C_1$—$C_8$ haloalkyl, $C_2$—$C_8$ alkenyl, and $C_2$—$C_8$ alkynyl | H, F, Cl, Br, CN, $OR^5$, $NR^5R^6$, $SR^5$, $COR^5$, $C_1$—$C_4$ alkyl, $C_1$—$C_4$ heteroalkyl, $C_1$—$C_4$ haloalkyl and $C_2$—$C_4$ alkenyl | H, F, Cl, Br, CN, $OR^5$, $C_1$—$C_8$ alkyl, $C_1$—$C_8$ heteroalkyl, and $C_1$—$C_8$ haloalkyl | H and F |
| $R_9$ | H, F, Cl, Br, I, $NO_2$, CN, $OR^5$, $NR^5R^6$, $SR^5$, $COR^5$, $CO_2R^5$, $CONR^5R^6$, $C_1$—$C_8$ alkyl, $C_1$—$C_8$ heteroalkyl, $C_1$—$C_8$ haloalkyl, $C_2$—$C_8$ alkenyl and $C_2$—$C_8$ alkynyl | H, F, Cl, Br, CN, $OR^5$, $NR^5R^6$, $SR^5$, $COR^5$, $C_1$—$C_4$ alkyl, $C_1$—$C_4$ heteroalkyl, $C_1$—$C_4$ haloalkyl and $C_2$—$C_4$ alkenyl | H, F, Cl, Br, CN, $OR^5$, $C_1$—$C_8$ alkyl, $C_1$—$C_8$ heteroalkyl, and $C_1$—$C_8$ haloalkyl | H and F |
| $R_{10}$ | H, F, Cl, Br, $OR^5$, $C_1$—$C_4$ alkyl, $C_1$—$C_4$ haloalkyl and $C_1$—$C_4$ heteroalkyl $R^{10}$ and $R^{14}$ taken together form a bond | H, F, Cl, $OR^5$, $C_1$—$C_4$ alkyl and $C_1$—$C_4$ haloalkyl | H, F, Cl, $CH_3$ and $CF_3$ | H and F |
| $R_{11}$ | H, F, Cl, Br, $OR^5$, $C_1$—$C_4$ alkyl, $C_1$—$C_4$ haloalkyl and $C_1$—$C_4$ heteroalkyl | H, F, Cl, $OR^5$, $C_1$—$C_4$ alkyl and $C_1$—$C_4$ haloalkyl | H, F, Cl, $CH_3$ and $CF_3$ | H and F |
| $R_{12}$ | H, F, Cl, Br, $OR^5$, $C_1$—$C_4$ alkyl, $C_1$—$C_4$ haloalkyl and $C_1$—$C_4$ heteroalkyl $R^{12}$ and $R^{14}$ taken together form a bond | H, F, Cl, $OR^5$, $C_1$—$C_4$ alkyl and $C_1$—$C_4$ haloalkyl | H, F, Cl, $CH_3$ and $CF_3$ | H and F |
| $R_{13}$ | H, F, Cl, Br, $OR^5$, $C_1$—$C_4$ alkyl, $C_1$—$C_4$ haloalkyl and $C_1$—$C_4$ heteroalkyl | H, F, Cl, $OR^5$, $C_1$—$C_4$ alkyl and $C_1$—$C_4$ haloalkyl | H, F, Cl, $CH_3$ and $CF_3$ | H and F |
| $R_{14}$ | H, F, Cl, Br, $OR^5$, $C_1$—$C_4$ alkyl, $C_1$—$C_4$ haloalkyl and $C_1$—$C_4$ heteroalkyl $R^{12}$ and $R^{14}$ taken together form a bond $R^{10}$ and $R^{14}$ taken together form a bond | H, F, Cl, $OR^5$, $C_1$—$C_4$ alkyl and $C_1$—$C_4$ haloalkyl | H, F, Cl, $CH_3$ and $CF_3$ | H and F |
| $R_{15}$ | H, F, Cl, Br, $OR^5$, $C_1$—$C_4$ alkyl, $C_1$—$C_4$ haloalkyl and $C_1$—$C_4$ heteroalkyl | H, F, Cl, $OR^5$, $C_1$—$C_4$ alkyl and $C_1$—$C_4$ haloalkyl | H, F, Cl, $CH_3$ and $CF_3$ | H and F |
| Y | O, S, $NR^6$ and $CR^{14}R^{15}$ | S and $CR^{14}R^{15}$ | S and $CH_2$ | S |
| Z | O, S, $NR^6$ and $CR^{14}R^{15}$ | S and $CR^{14}R^{15}$ | S and $CH_2$ | S |
| n | 0, 1, 2, or 3 | 0, 1, or 2 | 0 or 1 | 1 |

In one aspect, the present invention provides a pharmaceutical composition comprising an effective amount of a progesterone receptor modulator compound according to any one of formulae I and II shown above wherein $R^1$ through $R^{15}$, n, Y and Z all have the same definitions as given above.

In another aspect, the present invention comprises a method of modulating a process mediated by a progesterone receptor comprising administering to a patient having a condition mediated by a progesterone receptors an effective amount of a composition comprising a compound according to any one of the formulae I through II shown above, wherein $R^1$ through $R^{15}$, n, Y and Z all have the same definitions as those given above.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

PR modulator compounds of the present invention may be particularly useful for female hormone replacement therapy and as modulators of fertility (e.g., as contraceptives, contragestational agents or abortifacients, in vitro fertilization, pregnancy maintenance), either alone or in conjunction with one or more estrogen receptor modulators. PR modulator compounds of this invention also may be used in the treatment of dysfunctional uterine bleeding, dysmenorrhea, endometriosis, leiomyomas (uterine fibroids), hot flushes, mood disorders, and meningiomas. PR modulator compounds of this invention also may be used in the treatment of various hormone-dependent cancers, including, without limitation, cancers of ovaries, breast, endometrium and prostate. PR modulator compounds of this invention can also be used in treatment of female osteoporosis, either alone or in combination with one or more estrogen receptor modulators.

It will be understood by those skilled in the art that while the compounds of the present invention will typically be employed as a selective agonists, partial agonists or antagonists, there may be instances where a compound with a mixed steroid receptor profile is preferred. For example, use of a PR agonist (i.e., progestin) in female contraception often leads to the undesired effects of increased water retention and acne flare ups. In this instance, a compound that is primarily a PR agonist, but also displays some AR and MR modulating activity, may prove useful. Specifically, the mixed MR effects would be useful to control water balance in the body, while the AR effects would help to control any acne flare ups that occur.

Furthermore, it will be understood by those skilled in the art that the compounds of the present invention, typically pharmaceutical compositions and formulations containing one or more of these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative PR modulator compounds (i.e., agonists, partial agonists and antagonists) according to the present invention include:

9-Fluoro-5-(1,3-dithia-2-cyclohexylidene)-1,2-dihydro-2,2,4-trimethyl-5H-chromeno[3,4-f]quinoline (compound 10);

8-methoxy-5-(1,3-dithia-2-cyclohexylidene)-1,2-dihydro-2,2,4-trimethyl-5H-chromeno[3,4-f]quinoline (compound 13);

7,9-difluoro-5-(1,3-dithia-2-cyclohexylidene)-1,2-dihydro-2,2,4-trimethyl-5H-chromeno[3,4-f]quinoline (compound 15);

7-fluoro-5-(1,3-dithia-2-cyclohexylidene)-1,2-dihydro-2,2-dimethyl-5H-chromeno[3,4-f]quinoline (compound 17);

7-fluoro-5-cyclohexylidene-1,2-dihydro-2,2,4-trimethyl-5H-chromeno[3,4-f]quinoline (compound 19);

7,9-difluoro-5-cyclohexylidene-1,2-dihydro-2,2,4-trimethyl-5H-chromeno[3,4-f]quinoline (compound 20);

7-fluoro-5-(1,3-dithia-2-cyclohexylidene)-1,2-dihydro-2,2-dimethyl-5H-chromeno[3,4-f]quinoline (compound 21); and 7-fluoro-5-(2-cyclohexenylidene)-1,2-dihydro-2,2,4-trimethyl-5H-chromeno[3,4-f]quinoline (compound 23).

The sequence of steps for the general schemes to synthesize the compounds of the present invention is shown below. In each of the Schemes the R groups (e.g., $R^1$, $R^2$, etc.) correspond to the specific substitution patterns noted in the Examples. However, it will be understood by those skilled in the art that other functionalities disclosed herein at the indicated positions of compounds of formulae I and II also comprise potential substituents for the analogous positions on the structures within the Schemes. In a further aspect, the present invention contains a novel process for the preparation of the compounds of the present invention.

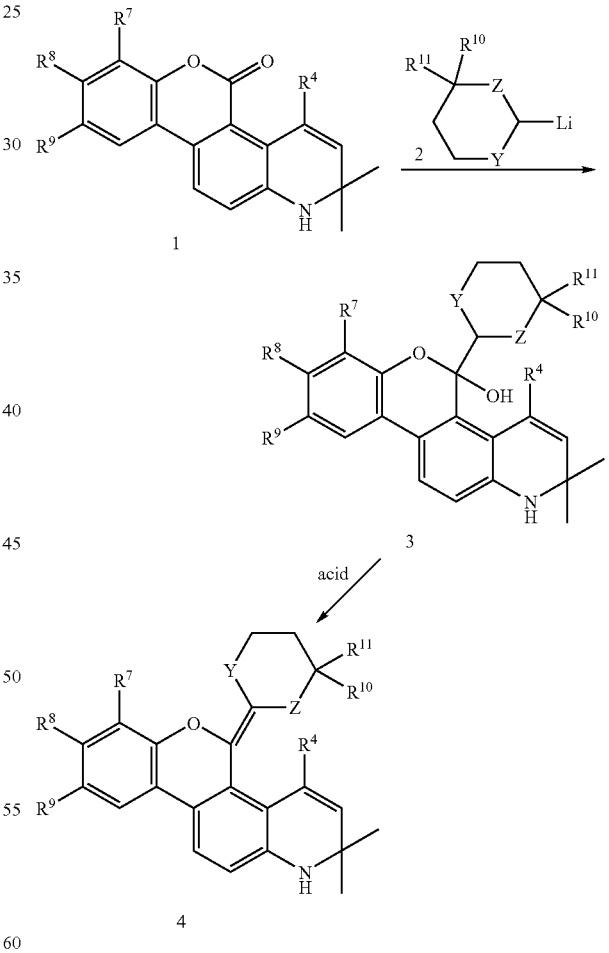

Scheme I

The process of Scheme I begins with addition of lithium reagents 2 to lactones 1 that were previously disclosed (Todd, Jones; et al. U.S. Pat. Nos. 5,693,646; 5,693,647 and 5,696,127) to produce hemiacetal 3. Treatment of the intermediate 3 with a Lewis acid, such as p-toluenesulfonic acid, affords the cyclic alkylidenes 4.

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, any of the PR modulator compounds of the present invention can be combined in a mixture with a pharmaceutically acceptable carrier to provide pharmaceutical compositions useful for treating the biological conditions or disorders noted herein in mammalian, and particularly in human patients. The particular carrier employed in these pharmaceutical compositions may take a wide variety of forms depending upon the type of administration desired. Suitable administration routes include enteral (e.g., oral), topical, suppository, inhalable and parenteral (e.g., intravenous, intramuscular and subcutaneous).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent a desirable oral dosage form for the pharmaceutical compositions of the present invention.

For parenteral administration, the carrier will typically comprise sterile water, although other ingredients that aid in solubility or serve as preservatives may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin and water in oil emulsions such as Eucerin™, available from Beiersdorf (Cincinnati, Ohio). Examples of suitable cream bases are Nivea™ Cream, available from Beiersdorf (Cincinnati, Ohio), cold cream (USP), Purpose␣CreaM™, available from Johnson & Johnson (New Brunswick, N.J.), hydrophilic ointment (USP) and Lubriderm™, available from Warner-Lambert (Morris Plains, N.J.).

The pharmaceutical compositions and compounds of the present invention will generally be administered in the form of a dosage unit (e.g., tablet, capsule, etc.). The compounds of the present invention generally are administered in a daily dosage of from about 1 µg/kg of body weight to about 50 mg/kg of body weight. Typically, the compounds of the present invention are administered in a daily dosage of from about 2 µg/kg to about 25 mg/kg of body weight. Most often, the compounds of the present invention are administered in a daily dosage of from about 10 µg/kg to about 5 mg/kg body weight. As recognized by those skilled in the art, the particular quantity of pharmaceutical composition according to the present invention administered to a patient will depend upon a number of factors, including, without limitation, the biological activity desired, the condition of the patient, and tolerance for the drug.

Compounds of this invention also have utility when radio- or isotopically-labeled as ligands for use in assays to determine the presence of PR in a cell background or extract. They may be particularly useful due to their ability to selectively activate progesterone receptors, and can therefore be used to determine the presence of such receptors in the presence of other steroid receptors or related intracellular receptors.

The compounds and pharmaceutical compositions of the present invention may be extremely potent activators of PR. For example, the compounds and compositions of the present invention may display 50% maximal activation of PR at a concentration of less than 50 nM. Some compounds and compositions of the present invention may display 50% maximal activation of PR at a concentration of less than 20 nM, and some may display such activity at a concentration of less than 10 nM.

The invention will be further illustrated by reference to the following non-limiting Examples.

EXAMPLE 1

Preparation of 9-Fluoro-5-(1,3-dithia-2-cyclohexylidene)-1,2-dihydro-2,2,4-trimethyl-5H-chromeno[3,4-f]quinoline (Compound 10, Structure 4 of Scheme I, where $R^4$=methyl, $R^7$=$R^8$=$R^{10}$=$R^{11}$=H, $R^9$=F, Y=Z=S)

To a solution of 1,3-dithiane (0.24 g, 2.0 mmol) in THF (10 mL) at −70° C. was added n-BuLi (1.6 M in hexane, 1.3 mL) and the resulting mixture was stirred at −10° C. for 2 h. To the reaction mixture at −70° C. was added 9-fluoro-1,2-dihydro-2,2,4-trimethyl-5-coumarino[3,4-f]quinoline (Compound 11, Structure 1 of Scheme I, where $R^4$=methyl, $R^7$=$R^8$=H, $R^9$=F) (0.12 g, 0.40 mmol) in THF (1 mL). The dark red solution was slowly warmed to −30° C. till the red color faded away and was quenched immediately with water. Extraction with EtOAc and chromatography afforded 9-fluoro-5-(1,3-dithia-2-cyclohexyl)-5-hydroxy-1,2-dihydro-2,2,4-trimethyl-5H-chromeno[3,4-f]quinoline (Compound 12, Structure 3 of Scheme I, where $R^4$=methyl, $R^7$=$R^8$=$R^{10}$=$R^{11}$=H, $R^9$=F, Y=Z=S), which was then treated in $CH_2Cl_2$ (10 mL) with catalytic amount of TsOH for 15 h. The reaction was quenched with aqueous carbonate and extracted with EtOAc. Chromatography provided compound 10 (70 mg, 42%) as a yellow solid: mp 120–122° C., $^1$H-NMR (400 MHz, CDCl$_3$) 7.34 (d, J=8.3, 1H), 7.32 (dd, J=9.7 and 2.9, 1H), 7.07 (dd, J=8.7 and 4.9, 1H), 6.84 (td, J=8.4 and 2.8, 1H), 6.62 (d, J=8.3, 1H), 5.48 (s, 1H), 4.17 (s, 1H), 3.02 (ddd, J=13.4, 8.2 and 5.1, 1H), 2.91–2.79 (m, 2H), 2.68 (dt, J=13.4 and 5.5, 1H), 2.20–2.04 (m, 2H), 1.99 (s, 3H), 1.41 (s, 3H) and 1.28 (s, 3H).

EXAMPLE 2

Preparation of 8-methoxy-5-(1,3-dithia-2-cyclohexylidene)-1,2-dihydro-2,2,4-trimethyl-5H-chromeno[3,4-f]quinoline (Compound 13, Structure 4 of Scheme I, where $R^4$=methyl, $R^7$=$R^9$=$R^{10}$=$R^{11}$=H, $R^8$=methoxy, Y=Z=S)

This compound was prepared in a similar fashion as that described in Example 1 from 1,3-dithiane and 8-methoxy-1,2-dihydro-2,2,4-trimethyl-5-coumarino[3,4-f]quinoline (Compound 14, Structure 1 of Scheme I, where $R^4$=methyl, $R^7$=$R^9$=H, $R^8$=methoxy) as a yellow solid: $^1$H-NMR (400 MHz, CDCl$_3$) 7.39 (d, J=8.2, 1H), 7.20 (d, J=2.9, 1H), 7.07 (d, J=8.9, 1H), 6.73 (dd, J=8.9, 2.9, 1H), 6.63 (d, J=8.2, 1H), 5.47 (s, 1H), 4.1 (bs, 1H), 3.82 (s, 3H), 3.04–2.98 (m, 1H), 2.89–2.78 (m, 2H), 2.68–2.64 (m, 1H), 2.16–2.03 (m, 2H), 1.99 (s, 3H)1.41 (s, 3H), 1.25 (s, 3H).

EXAMPLE 3

Preparation of 7,9-difluoro-5-(1,3-dithia-2-cyclohexylidene)-1,2-dihydro-2,2,4-trimethyl-5H-chromeno[3,4-f]quinoline (Compound 15, Structure 4 of Scheme I, where $R^4$=methyl, $R^8$=$R^{10}$=$R^{11}$=H, $R^7$, $R^9$=fluorine, Y=Z=S)

This compound was prepared in a similar fashion as that described in Example 1 from 1,3-dithiane and 7,9-difluoro-1,2-dihydro-2,2,4-trimethyl-5-coumarino[3,4-f]quinoline (Compound 16, Structure 1 of Scheme I, where $R^4$=methyl, $R^7$=$R^9$=fluorine, $R^8$=H) as a yellow solid: $^1$H-NMR (500 MHz, CDCl$_3$) 7.31 (d, J=8.2, 1H), 7.14–7.11 (m, 1H), 6.72 (ddd, J=10.1, 8.2, 2.7, 1H), 6.62 (d, J=8.2, 1H), 5.48 (s, 1 H), 4.18 (bs, 1H), 3.07–3.01 (m, 1H), 2.92–2.82 (m, 2H), 2.72–2.67 (m, 1H), 2.18–2.07 (m, 2H), 1.99 (d, J=1.2, 3H), 1.41 (s, 3H), 1.28 (s, 3H).

EXAMPLE 4

Preparation of 7-fluoro-5-(1,3-dithia-2-cyclohexylidene)-1,2-dihydro-2,2,4-trimethyl-5H-chromeno[3,4-f]quinoline (Compound 17, Structure 4 of Scheme I, where $R^4$=methyl, $R^8$=$R^9$=$R^{10}$=$R^{11}$=H, $R^7$=fluorine, Y=Z=S)

This compound was prepared in a similar fashion as that described in Example 1 from 1,3-dithiane and 7-fluoro-1,2-dihydro-2,2,4-trimethyl-5-coumarino[3,4-f]quinoline (Compound 18, Structure 1 of Scheme I, where $R^4$=methyl, $R^7$=fluorine, $R^8$=$R^9$=H) as a yellow solid: $^1$H-NMR (500 MHz, CDCl$_3$) 7.44–7.42 (m, 1H), 7.42 (d, J=8.2, 1H), 6.98–6.94 (m, 2H), 6.64 (d, J=8.2, 1H), 5.49 (d, J=1.5, 1H), 4.14 (bs, 1H), 3.08–3.02 (m, 1H), 2.93–2.82 (m, 2H), 2.72–2.66 (m, 1H), 2.18–2.06 (m, 2H), 2.01 (d, J=1.2, 3H), 1.42 (s, 3H), 1.29 (s, 3H).

EXAMPLE 5

Preparation of 7-fluoro-5-cyclohexylidene-1,2-dihydro-2,2,4-trimethyl-5H-chromeno[3,4-f]quinoline (Compound 19, Structure 4 of Scheme I, where $R^4$=methyl, $R^8$=$R^9$=$R^{10}$=$R^{11}$=H, $R^7$=fluorine, Y=Z=CH$_2$)

This compound was prepared in a similar fashion as that described in Example 1 from cyclohexylithium and 7-fluoro-1,2-dihydro-2,2,4-trimethyl-5-coumarino[3,4-f]quinoline (Compound 18, Structure 1 of Scheme I, where $R^4$=methyl, $R^7$=fluorine, $R^8$=$R^9$=H) as a yellow solid: $^1$H-NMR (500 MHz, CDCl$_3$) 7.43–7.40 (m, 1H), 7.41 (d, J=8.2, 1 H), 6.96–6.86 (m, 2H), 6.61 (d, J=8.2, 1H), 5.45 (s, 1 H), 4.07 (bs, 1H), 3.03 (ddd, J=14.0, 4.9, 4.9, 1H), 2.21–2.08 (m, 2H), 1.99 (d, J=1.2, 3H), 1.92–1.86 (m, 1H), 1.76–1.70 (m, 1H), 1.62–1.57 (m, 2H), 1.45–1.24 (m, 3H), 1.40 (s, 3H), 1.18 (s, 3H).

EXAMPLE 6

Preparation of 7,9-difluoro-5-cyclohexylidene-1,2-dihydro-2,2,4-trimethyl-5H-chromeno[3,4-f]quinoline (Compound 20, Structure 4 of Scheme I, where $R^8$=$R^{10}$=$R^{11}$=H, $R^4$=methyl, $R^7$=$R^9$=fluorine, Y=Z=CH$_2$)

This compound was prepared in a similar fashion as that described in Example 1 from cyclohexylithium and 7,9-difluoro-1,2-dihydro-2,2,4-trimethyl-5-coumarino[3,4-f]quinoline (Compound 16, Structure 1 of Scheme I, where $R^4$=methyl, $R^7$=$R^9$=fluorine, $R^8$=H) as a yellow solid: $^1$H-NMR (500 MHz, CDCl$_3$) 7.32 (d, J=8.2, 1H), 7.14–7.11 (m, 1H), 6.70 (ddd, J=10.4, 8.5, 2.8, 1H), 6.61 (d, J=8.2, 1H), 5.45 (s, 1H), 4.12 (bs, 1H), 3.05–3.01 (m, 2H), 2.20–2.08 (m, 2H), 1.97 (d, J=1.2, 3H), 1.91–1.85 (m, 1H), 1.78–1.71 (m, 1H), 1.63–1.58 (m, 2H), 1.45–1.23 (m, 3H), 1.40 (s, 3H), 1.18 (s, 3H).

EXAMPLE 7

Preparation of 7-fluoro-5-(1,3-dithia-2-cyclohexylidene)-1,2-dihydro-2,2-dimethyl-5H-chromeno[3,4-f]quinoline (Compound 21, Structure 4 of Scheme I, where $R^4$=$R^8$=$R^9$=$R^{10}$=$R^{11}$=H, $R^7$=fluorine, Y=Z=S)

This compound was prepared in a similar fashion as that described in Example 1 from 1,3-dithiane and 7-fluoro-1,2-dihydro-2,2-dimethyl-5-coumarino[3,4-f]quinoline (Compound 22, Structure 1 of Scheme I, where $R^7$=fluorine, $R^4$=$R^8$=$R^9$=H) as a yellow solid: $^1$H-NMR (500 MHz, CDCl$_3$) 7.39–7.36 (m, 1H), 7.36 (d, J=8.2, 1H), 6.96–6.93 (m, 2H), 6.55 (d, J=8.8, 1H), 6.31 (d, J=10.1, 1H), 5.59 (d, J=9.8, 1H), 4.0 (bs, 1H), 3.14–3.07 (m, 1H), 2.96–2.84 (m, 2H), 2.80–2.74 (m, 1H), 2.22–2.08 (m, 2H), 1.42 (s, 3H), 1.32 (s, 3H).

EXAMPLE 8

Preparation of 7-fluoro-5-(2-cyclohexenylidene)-1,2-dihydro-2,2,4-trimethyl-5H-chromeno[3,4-f]quinoline (Compound 23, Structure 4 of Scheme I, where $R^4$=methyl, $R^8$=$R^9$=$R^{11}$=H, $R^7$=fluorine, $R^{10}$/$R^{14}$=a bond, Z=CHR$^{14}$, Y=CH$_2$)

This compound was prepared in a similar fashion as that described in Example 1 from cyclohexenylithium and lactone 18 (Structure 1 of Scheme I, where $R^4$=methyl, $R^7$=fluorine, $R^8$=$R^9$=H) as a yellow solid: $^1$H-NMR (500 MHz, Acetone-d$_6$) 7.57–7.54 (m, 1H), 7.54 (d, J=8.2, 1H), 7.04–6.97 (m, 2H), 6.77 (d, J=8.2, 1H), 6.11 (ddd, J=10.1, 2.1, 1.8, 1H), 5.84–5.79 (m, 2H), 5.45 (s, 1H), 2.96–2.88 (m, 2H), 2.61–2.55 (m, 1H), 2.20–2.13 (m, 1H), 1.93 (d, J=1.2, 3H), 1.81–1.70 (m, 2H), 1.40 (s, 3H), 1.21 (s, 3H).

The activity of selected steroid receptor modulator compounds of the present invention were evaluated utilizing the cotransfection assay, and in standard receptor competitive binding assays, according to the following illustrative Examples.

EXAMPLE 9

Cotransfection Assay

The function and detailed preparation procedure of the cotransfection assays have been described previously (Pathirana, Mol. Pharm. 1995, 47, 630–635). Briefly, the cotransfection assays were carried out in CV-1 cells (African green monkey kidney fibroblasts), which were transiently transfected, by the standard calcium phosphate coprecipitation procedure (Berger, et al., J. Steroid Biochem. Mol. Bio. 1992, 41, 733–738) with the Plasmid containing receptor, MTV-LUC reporter, pRS-β-Gal, and filler DNA (Rous sarcoma virus chloramphenicol acetyltransferase). The agonist activity was determined by examining the LUC expression (normalized response) and the efficacy readout was a relative value to the maximal LUC expression produced by progesterone. All the cotransfection experiments were carried out in 96-well plates by automation (Beckman Biomomek automated workstation).

Receptor Binding Assays

The preparation of receptor binding assays for hPR-A was described in literature (Pathirana, et al., *Mol. Pharm.* 1995, 47, 630–635.)

The agonist, antagonist and binding activity assay results of selected progesterone receptor modulator compounds of the present invention and the standard reference compounds on PR are shown in Table 1 below. Efficacy is reported as the percent maximal response observed for each compound relative to the reference agonist and antagonist compounds indicated above. Also reported in Table 1 for each compound is its antagonist potency or $IC_{50}$ (which is the concentration (nM), required to reduce the maximal response by 50%), and its agonist potency or $EC_{50}$ (nM), which is the effective concentration that produced 50% of the maximum response.

TABLE 1

Agonist, antagonist and binding activity of progesterone receptor modulator compounds of present invention and the reference agonist compound, progesterone (Prog), and reference antagonists compound, RU486 and ZK299.

| Cmpd No. | PR Agonist CV-1 Cells | | PR Antagonist CV-1 Cells | | PR Binding $K_i$ (nM) |
|---|---|---|---|---|---|
| | Efficacy (%) | Potency (nM) | Efficacy (%) | Potency (nM) | |
| Prog | 100 | 2.9 | na | na | 3.5 |
| RU486 | na | na | 96 | 0.18 | 0.58 |
| ZK299 | na | na | 99 | 1.6 | 18 |
| 10 | 144 | 2.0 | na | na | 6.3 |
| 13 | 56 | 32 | na | na | 14 |
| 15 | 155 | 5.3 | na | na | 3.7 |
| 17 | 107 | 11 | na | na | 4.3 |
| 19 | 48 | 38 | nt | nt | 74 |
| 20 | 82 | 16 | na | na | 39 |
| 21 | 45 | 32 | nt | nt | nt |
| 23 | 70 | 35 | na | na | 22 | na = not active (i.e. efficacy of <20 and potency of >1,000)
nt = not tested

Pharmacological and other Applications

The following Example provides illustrative pharmaceutical composition formulations:

EXAMPLE 10

Hard gelatin capsules are prepared using the following ingredients:

| | Quantity (mg/capsule) |
|---|---|
| COMPOUND 10 | 16 |
| Starch, dried | 100 |
| Magnesium stearate | 10 |
| Total | 120 mg |

The above ingredients are mixed and filled into hard gelatin capsules in 120 mg quantities.

A tablet is prepared using the ingredients below:

| | Quantity (mg/tablet) |
|---|---|
| COMPOUND 10 | 10 |
| Cellulose, microcrystalline | 200 |
| Silicon dioxide, fumed | 10 |
| Stearic acid | 10 |
| Total | 230 mg |

The components are blended and compressed to form tablets each weighing 230 mg.

Tablets, each containing 10 mg of active ingredient, are made as follows:

| | Quantity (mg/tablet) |
|---|---|
| COMPOUND 10 | 10 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 100 mg |

The active ingredient, starch and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate and talc, previously passed through a No. 60 mesh U.S. sieve are then added to the granules which, after mixing, are compressed on a tablet machine to yield tablets each weighing 150 mg.

Suppositories, each containing 225 mg of active ingredient, may be made as follows:

| | Quantity (mg/suppository) |
|---|---|
| COMPOUND 10 | 20 |
| Saturated fatty acid glycerides | 2,000 |
| Total | 2,020 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| | Quantity |
|---|---|
| COMPOUND 10 | 10 mg |
| isotonic saline | 1000 mL |
| glycerol | 100 mL |

The compound is dissolved in the glycerol and then the solution is slowly diluted with isotonic saline. The solution of the above ingredients is then administered intravenously at a rate of 1 mL per minute to a patient.

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

The scope of the invention is not to be limited by the description of the examples. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

What is claimed is:

1. A compound of the formula:

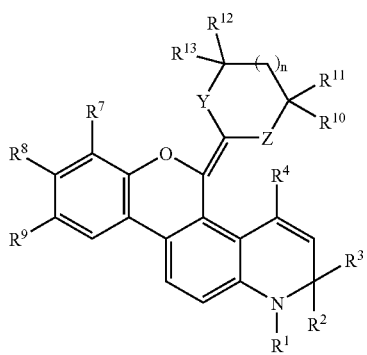

(I)

wherein:
R$^1$ is selected from the group of hydrogen, C$_1$–C$_4$ alkyl, C$_1$–C$_4$ haloalkyl, C$_1$–C$_4$ heteroalkyl, COR$^5$, CO$_2$R$^5$, SO$_2$R$^5$, and CONR$^5$R$^6$;

R$^2$ and R$^3$ each independently is selected from the group of hydrogen, C$_1$–C$_6$ alkyl, and C$_1$–C$_6$ haloalkyl; or R$^2$ and R$^3$ taken together form a cycloalkyl ring of from three to twelve carbons;

R$^4$ is selected from the group of hydrogen, F, Cl, Br, CN, OR$^5$, C$_1$–C$_4$ alkyl, C$_1$–C$_4$ haloalkyl, and C$_1$–C$_4$ heteroalkyl;

R$^5$ and R$^6$ each is independently selected from the group of hydrogen, C$_1$–C$_4$ alkyl, C$_1$–C$_4$ heteroalkyl, and C$_1$–C$_4$ haloalkyl;

R$_7$ through R$_9$ each independently is selected from the group of hydrogen, F, Cl, Br, I, NO$_2$, CN, OR$^5$, NR$^5$R$^6$, SR$^5$, COR$^5$, CO$_2$R$^5$, CONR$^5$R$^6$, C$_1$–C$_8$ alkyl, C$_1$–C$_8$ heteroalkyl, C$_1$–C$_8$ haloalkyl, C$_2$–C$_8$ alkenyl, C$_2$–C$_8$ alkynyl;

R$^{10}$ through R$^{15}$ each independently is selected from the group of hydrogen, F, Cl, Br, OR$^5$, C$_1$–C$_4$ alkyl, C$_1$–C$_4$ haloalkyl, and C$_1$–C$_4$ heteroalkyl; or R$^{12}$ and R$^{14}$ taken together form a bond, when Y is CR$^{14}$R$^{15}$; or R$^{10}$ and R$^{14}$ taken together form a bond, when Z is CR$^{14}$R$^{15}$;

Y and Z each independently is selected from the group of O, S, NR$^6$ and CR$^{14}$R$^{15}$; and n is 0, 1, 2, or 3;

or a pharmaceutically acceptable salt thereof.

2. A compound of the formula:

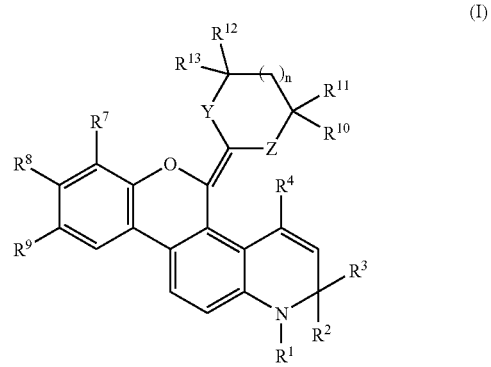

(I)

wherein:
R$^1$ is selected from the group of hydrogen, C$_1$–C$_4$ alkyl, COR$^5$, CO$_2$R$^5$, and SO$_2$R$^5$;

R$^2$ and R$^3$ each independently is selected from the group of C$_1$–C$_4$ alkyl;

R$^4$ is selected from the group of hydrogen, F, Cl, Br, C$_1$–C$_4$ alkyl, and C$_1$–C4 haloalkyl;

R$^5$ and R$^6$ each is independently selected from the group of hydrogen, and C$_1$–C$_4$ alkyl;

R$^7$ through R$^9$ each independently is selected from the group of hydrogen, F, Cl, Br, CN, OR$^5$, C$_1$–C$_8$ alkyl, C$_1$–C$_8$ heteroalkyl, and C$_1$–C$_8$ haloalkyl;

R$^{10}$ through R$^{15}$ each independently is selected from the group of hydrogen, F, Cl, OR$^5$, C$_1$–C$_4$ alkyl, C$_1$–C$_4$ haloalkyl; or R$^{12}$ and R$^{14}$ taken together form a bond, when Y is CR$^{14}$R$^{15}$; or R$^{10}$ and R$^{14}$ taken together form a bond, when Z is CR$^{14}$R$^{15}$;

Y and Z each independently is selected from the group of S, and CR$^{14}$R$^{15}$; and n is 0, 1, or 2;

or a pharmaceutically acceptable salt thereof.

3. A compound according to claim 2, wherein
R$^1$ is hydrogen;
R$^2$ and R$^3$ is CH$_3$;
R$^4$ is selected from the group of F, Cl, Br, CH$_3$, and CF$_3$;
R$^7$ is hydrogen or F;
R$^8$ is selected from the group of H, CH$_3$, OH, and OCH$_3$;
R$^9$ is selected from the group of hydrogen, F, Cl, Br, CN, OCH$_3$, CH$_3$, and CF$_3$;
R$^{10}$, R$^{11}$, R$^{13}$, R$^{15}$ each independently is selected from the group of hydrogen, F, Cl, CH$_3$, and CF$_3$; and
R$^{12}$ and R$^{14}$ taken together form a bond, when Y is CR$^{14}$R$^{15}$.

4. compound according to claim 1, wherein said compound is selected from the group of:
9-Fluoro-5-(1,3-dithia-2-cyclohexylidene)-1,2-dihydro-2,2,4-trimethyl-5H-chromeno[3,4-f]quinoline (compound 10);
8-methoxy-5-(1,3-dithia-2-cyclohexylidene)-1,2-dihydro-2,2,4-trimethyl-5H-chromeno[3,4-f]quinoline (compound 13);
7,9-difluoro-5-(1,3-dithia-2-cyclohexylidene)-1,2-dihydro-2,2,4-trimethyl-5H-chromeno[3,4-f]quinoline (compound 15);

7-fluoro-5-(1,3-dithia-2-cyclohexylidene)-1,2-dihydro-2, 2,4-trimethyl-5H-chromeno[3,4-f]quinoline (compound 17);
7-fluoro-5-cyclohexylidene-1,2-dihydro-2,2,4-trimethyl-5H-chromeno[3,4-f]quinoline (compound 19);
7,9-difluoro-5-cyclohexylidene-1,2-dihydro-2,2,4-trimethyl-5H-chromeno[3,4-f]-quinoline (compound 20);
7-fluoro-5-(1,3-dithio-2-cyclohexylidene)-1,2-dihydro-2, 2-dimethyl-5H-chromeno[3,4-f]quinoline (compound 21); and
7-fluoro-5-(2-cyclohexenylidene)-1,2-dihydro-2,2,4-trimethyl-5H-chromeno[3,4-f]-quinoline (compound 23).

5. A compound of the formula:

(II)

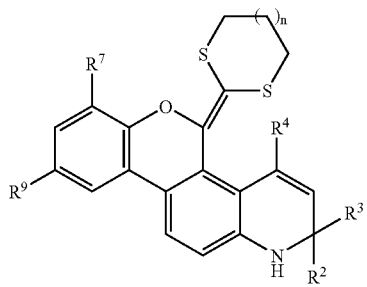

wherein:
$R^2$ and $R^3$ each independently is selected from the group of $C_1$–$C_4$ alkyl, and $C_1$–$C_4$ haloalkyl;
$R^4$ is selected from the group of hydrogen, F, Cl, Br, CN, $OR^5$, $C_1$–$C_4$ alkyl, $C_1$–$C_4$ haloalkyl, and $C_1$–$C_4$ heteroalkyl;
$R^5$ is selected from the group of hydrogen, $C_1$–$C_4$ alkyl, $C_1$–$C_4$ heteroalkyl, and $C_1$–$C_4$ haloalkyl;
$R^7$ and $R^9$ each independently is selected from the group of hydrogen, F, Cl, Br, CN, $OR^5$, $NR^5R^6$, $SR^5$, $COR^5$, $C_1$–$C_4$ alkyl, $C_1$–$C_4$ heteroalkyl, $C_1$–$C_4$ haloalkyl, $C_2$–$C_4$ alkenyl;
n is 0, 1, 2, or 3;
or a pharmaceutically acceptable salt thereof.

6. A compound of the formula:

(II)

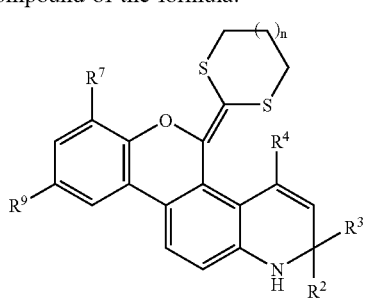

wherein:
$R^2$ and $R^3$ are $CH_3$;
$R^4$ is selected from the group of F, Cl, Br, $CH_3$, and $CF_3$;
$R^5$ is selected from the group of hydrogen, $C_1$–$C_4$ alkyl, $C_1$–$C_4$ heteroalkyl, and $C_1$–$C_4$ haloalkyl;
$R^7$ is hydrogen or F;
$R^9$ selected from the group of hydrogen, F, Cl, Br, CN, $OCH_3$, $CH_3$, and $CF_3$;
n is 0, 1, 2 or 3;
or a pharmaceutically acceptable salt thereof.

7. A pharmaceutical composition comprising a pharmaceutically acceptable carrier and a compound of formula:

(I)

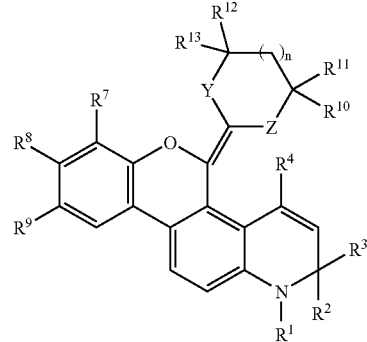

wherein:
$R^1$ is selected from the group of hydrogen, $C_1$–$C_4$ alkyl, $C_1$–$C_4$ haloalkyl, $C_1$–$C_4$ heteroalkyl, $COR^5$, $CO_2R^5$, $SO_2R^5$, and $CONR^5R^6$;
$R^2$ and $R^3$ each independently is selected from the group of hydrogen, $C_1$–$C_6$ alkyl, and $C_1$–$C_6$ haloalkyl; or
$R^2$ and $R^3$ taken together form a cycloalkyl ring of from three to twelve carbons;
$R^4$ is selected from the group of hydrogen, F, Cl, Br, CN, $OR^5$, $C_1$–$C_4$ alkyl, $C_1$–$C_4$ haloalkyl, and $C_1$–$C_4$ heteroalkyl;
$R^5$ and $R^6$ each is independently selected from the group of hydrogen, $C_1$–$C_4$ alkyl, $C_1$–$C_4$ heteroalkyl, and $C_1$–$C_4$ haloalkyl;
$R^7$ through $R^9$ each independently is selected from the group of hydrogen, F, Cl, Br, I, $NO_2$, CN, $OR^5$, $NR^5R^6$, $SR^5$, $COR^5$, $CO_2R^5$, $CONR^5R^6$, $C_1$–$C_8$ alkyl, $C_1$–$C_8$ heteroalkyl, $C_1$–$C_8$ haloalkyl, $C_2$–$C_8$ alkenyl, $C_2$–$C_8$ alkynyl;
$R^{10}$ through $R^{15}$ each independently is selected from the group of hydrogen, F, Cl, Br, $OR^5$, $C_1$–$C_4$ alkyl, $C_1$–$C_4$ haloalkyl, and $C_1$–$C_4$ heteroalkyl; or
$R^{12}$ and $R^{14}$ taken together form a bond, when Y is $CR^{14}R^{15}$; or
$R^{10}$ and $R^{14}$ taken together form a bond, when Z is $CR^{14}R^{15}$;
Y and Z each independently is selected from the group of O, S, $NR^6$ and $CR^{14}R^{15}$;
n is 0, 1, 2, or 3;
or a pharmaceutically acceptable salt thereof.

8. A pharmaceutical composition comprising a pharmaceutically acceptable carrier and a compound of formula:

(I)

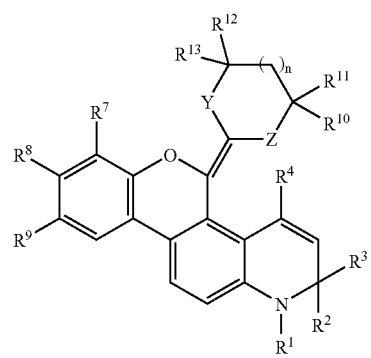

wherein:
$R^1$ is selected from the group of hydrogen, $C_1$–$C_4$ alkyl, $COR^5$, $CO_2R^5$, and $SO_2R^5$;

$R^2$ and $R^3$ each independently is selected from the group of $C_1$–$C_4$ alkyl;

$R^4$ is selected from the group of hydrogen, F, Cl, Br, $C_1$–$C_4$ alkyl, and $C_1$–$C_4$ haloalkyl;

$R^5$ and $R^6$ each is independently selected from the group of hydrogen, and $C_1$–$C_4$ alkyl;

$R^7$ through $R^9$ each independently is selected from the group of hydrogen, F, Cl, Br, CN, $OR^5$, $C_1$–$C_8$ alkyl, $C_1$–$C_8$ heteroalkyl, and $C_1$–$C_8$ haloalkyl;

$R^{10}$ through $R^{15}$ each independently is selected from the group of hydrogen, F, Cl, $OR^5$, $C_1$–$C_4$ alkyl, $C_1$–$C_4$ haloalkyl; or $R^{12}$ and $R^{14}$ taken together form a bond, when Y is $CR^{14}R^{15}$; or $R^{10}$ and $R^{14}$ taken together form a bond, when Z is $CR^{14}R^{15}$;

Y and Z independently is selected from the group of S, and $CR^{14}R^{15}$; and n is 0, 1, or 2;

or a pharmaceutically acceptable salt thereof.

9. A pharmaceutical composition according to claim 8, wherein $R^1$ is hydrogen;

$R^2$ and $R^3$ is $CH_3$;

$R^4$ is selected from the group of F, Cl, Br, $CH_3$, and $CF_3$;

$R^7$ is hydrogen or F;

$R^8$ is selected from the group of H, $CH_3$, OH, and $OCH_3$;

$R^9$ selected from the group of hydrogen, F, Cl, Br, CN, $OCH_3$, $CH_3$, and $CF_3$;

$R^{10}$, $R^{11}$, $R^{13}$, $R^{15}$ each independently is selected from the group of hydrogen, F, Cl, $CH_3$, and $CF_3$; and $R^{12}$ and $R^{14}$ taken together form a bond, when Y is $CR^{14}R^{15}$.

10. A compound according to claim 1, wherein $R^2$ and $R^3$ each independently is selected from the group of hydrogen, $C_1$–$C_6$ alkyl, and $C_1$–$C_6$ haloalkyl.

11. A pharmaceutical composition according to claim 7, wherein $R^2$ and $R^3$ each independently is selected from the group of hydrogen, $C_1$–$C_6$ alkyl, and $C_1$–$C_6$ haloalkyl.

* * * * *

UNITED STATES PATENT AND TRADEMARK OFFICE
CERTIFICATE OF CORRECTION

| | | |
|---|---|---|
| PATENT NO. | : 7,084,151 B2 | Page 1 of 6 |
| APPLICATION NO. | : 10/684227 | |
| DATED | : August 1, 2006 | |
| INVENTOR(S) | : Lin Zhi et al. | |

It is certified that error appears in the above-identified patent and that said Letters Patent is hereby corrected as shown below:

IN THE TITLE PAGES:

In Item [56] References Cited, in OTHER PUBLICATIONS:
in Tegley et al., please replace "Dihydrochromemo" with --Dihydrochromeno--
in Crombie et al., please replace "behavior" with --behaviour--

IN THE SPECIFICATION:

At column 6, in Table A, row 1, please replace "$R_1$" with --$R^1$--
at column 6, in Table A, row 2, please replace "$R_2$" with --$R^2$--
at column 6, in Table A, row 4, please replace "$R_3$" with --$R^3$--
at column 6, in Table A, row 6, please replace "$R_4$" with --$R^4$--
at column 6, in Table A, row 7, please replace "$R_5$" with --$R^5$--
at column 6, in Table A, row 8, please replace "$R_6$" with --$R^6$--
at column 6, in Table A, row 9, please replace "$R_7$" with --$R^7$--
at column 7, in Table A, row 10, please replace "$R_8$" with --$R^8$--
at column 7, in Table A, row 11, please replace "$R_9$" with --$R^9$--
at column 7, in Table A, row 12, please replace "$R_{10}$" with --$R^{10}$--
at column 7, in Table A, row 14, please replace "$R_{11}$" with --$R^{11}$--
at column 7, in Table A, row 15, please replace "$R_{12}$" with --$R^{12}$--
at column 7, in Table A, row 17, please replace "$R_{13}$" with --$R^{13}$--
at column 7, in Table A, row 18, please replace "$R_{14}$" with --$R^{14}$--
at column 7, in Table A, row 21, please replace "$R_{15}$" with --$R^{15}$--
at column 15, line 58, please replace "16" with --10--

IN THE CLAIMS:
Please replace Claims 1, 2, 4, 6, 8, and 9 with the following Claims:

Col. 17, Line 20-67
1. A compound of the formula:

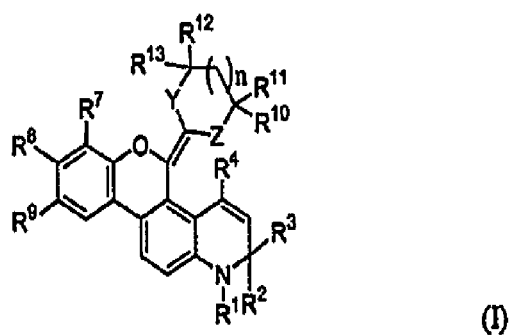

(I)

UNITED STATES PATENT AND TRADEMARK OFFICE
CERTIFICATE OF CORRECTION

PATENT NO. : 7,084,151 B2
APPLICATION NO. : 10/684227
DATED : August 1, 2006
INVENTOR(S) : Lin Zhi et al.

It is certified that error appears in the above-identified patent and that said Letters Patent is hereby corrected as shown below:

wherein:
- $R^1$ is selected from the group of hydrogen, $C_1$–$C_4$ alkyl, $C_1$–$C_4$ haloalkyl, $C_1$–$C_4$ heteroalkyl, $COR^5$, $CO_2R^5$, $SO_2R^5$, and $CONR^5R^6$;
- $R^2$ and $R^3$ each independently is selected from the group of hydrogen, $C_1$–$C_6$ alkyl, and $C_1$–$C_6$ haloalkyl; or
- $R^2$ and $R^3$ taken together form a cycloalkyl ring of from three to twelve carbons;
- $R^4$ is selected from the group of hydrogen, F, Cl, Br, CN, $OR^5$, $C_1$–$C_4$ alkyl, $C_1$–$C_4$ haloalkyl, and $C_1$–$C_4$ heteroalkyl;
- $R^5$ and $R^6$ each is independently selected from the group of hydrogen, $C_1$–$C_4$ alkyl, $C_1$–$C_4$ heteroalkyl, and $C_1$–$C_4$ haloalkyl;
- $R^7$ through $R^9$ each independently is selected from the group of hydrogen, F, Cl, Br, I, $NO_2$, CN, $OR^5$, $NR^5R^6$, $SR^5$, $COR^5$, $CO_2R^5$, $CONR^5R^6$, $C_1$–$C_8$ alkyl, $C_1$–$C_8$ heteroalkyl, $C_1$–$C_8$ haloalkyl, $C_2$–$C_8$ alkenyl, $C_2$–$C_8$ alkynyl;
- $R^{10}$ through $R^{15}$ each independently is selected from the group of hydrogen, F, Cl, Br, $OR^5$, $C_1$–$C_4$ alkyl, $C_1$–$C_4$ haloalkyl, and $C_1$–$C_4$ heteroalkyl; or
- $R^{12}$ and $R^{14}$ taken together form a bond, when Y is $CR^{14}R^{15}$; or
- $R^{10}$ and $R^{14}$ taken together form a bond, when Z is $CR^{14}R^{15}$;
- Y and Z each independently is selected from the group of O, S, $NR^6$ and $CR^{14}R^{15}$; and n is 0, 1, 2, or 3;

or a pharmaceutically acceptable salt thereof.

Col. 18, line 1–56
2. A compound of the formula:

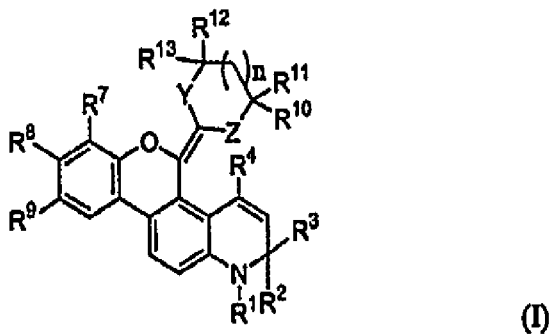

(I)

UNITED STATES PATENT AND TRADEMARK OFFICE
CERTIFICATE OF CORRECTION

PATENT NO. : 7,084,151 B2
APPLICATION NO. : 10/684227
DATED : August 1, 2006
INVENTOR(S) : Lin Zhi et al.

It is certified that error appears in the above-identified patent and that said Letters Patent is hereby corrected as shown below:

wherein:
- $R^1$ is selected from the group of hydrogen, $C_1$–$C_4$ alkyl, $COR^5$, $CO_2R^5$, and $SO_2R^5$;
- $R^2$ and $R^3$ each independently is selected from the group of $C_1$–$C_4$ alkyl;
- $R^4$ is selected from the group of hydrogen, F, Cl, Br, $C_1$–$C_4$ alkyl, and $C_1$–$C_4$ haloalkyl;
- $R^5$ and $R^6$ each is independently selected from the group of hydrogen, and $C_1$-$C_4$ alkyl;
- $R^7$ through $R^9$ each independently is selected from the group of hydrogen, F, Cl, Br, CN, $OR^5$, $C_1$–$C_8$ alkyl, $C_1$–$C_8$ heteroalkyl, and $C_1$–$C_8$ haloalkyl;
- $R^{10}$ through $R^{15}$ each independently is selected from the group of hydrogen, F, Cl, $OR^5$, $C_1$–$C_4$ alkyl, $C_1$–$C_4$ haloalkyl; or
- $R^{12}$ and $R^{14}$ taken together form a bond, when Y is $CR^{14}R^{15}$; or
- $R^{10}$ and $R^{14}$ taken together form a bond, when Z is $CR^{14}R^{15}$;
- Y and Z each independently is selected from the group of S, and $CR^{14}R^{15}$; and
- n is 0, 1, or 2;

or a pharmaceutically acceptable salt thereof.

Col. 18-19 line 56-14
4. A compound according to claim 1, wherein said compound is selected from the group of:
- 9-Fluoro-5-(1,3-dithia-2-cyclohexylidene)-1,2-dihydro-2,2,4-trimethyl-5*H*-chromeno[3,4-*f*]quinoline (compound 10);
- 8-methoxy-5-(1,3-dithia-2-cyclohexylidene)-1,2-dihydro-2,2,4-trimethyl-5*H*-chromeno[3,4-*f*]quinoline (compound 13);
- 7,9-difluoro-5-(1,3-dithia-2-cyclohexylidene)-1,2-dihydro-2,2,4-trimethyl-5*H*-chromeno[3,4-*f*]quinoline (compound 15);
- 7-fluoro-5-(1,3-dithia-2-cyclohexylidene)-1,2-dihydro-2,2,4-trimethyl-5*H*-chromeno[3,4-*f*]quinoline (compound 17);
- 7-fluoro-5-cyclohexylidene-1,2-dihydro-2,2,4-trimethyl-5*H*-chromeno[3,4-*f*]quinoline (compound 19);
- 7,9-difluoro-5-cyclohexylidene-1,2-dihydro-2,2,4-trimethyl-5*H*-chromeno[3,4-*f*]-quinoline (compound 20);
- 7-fluoro-5-(1,3-dithia-2-cyclohexylidene)-1,2-dihydro-2,2-dimethyl-5*H*-chromeno[3,4-*f*]quinoline (compound 21); and
- 7-fluoro-5-(2-cyclohexenylidene)-1,2-dihydro-2,2,4-trimethyl-5*H*-chromeno[3,4-*f*]-quinoline (compound 23).

UNITED STATES PATENT AND TRADEMARK OFFICE
CERTIFICATE OF CORRECTION

PATENT NO. : 7,084,151 B2  
APPLICATION NO. : 10/684227  
DATED : August 1, 2006  
INVENTOR(S) : Lin Zhi et al.

Page 4 of 6

It is certified that error appears in the above-identified patent and that said Letters Patent is hereby corrected as shown below:

Col. 19 Line 43-64  
6. A compound of the formula:

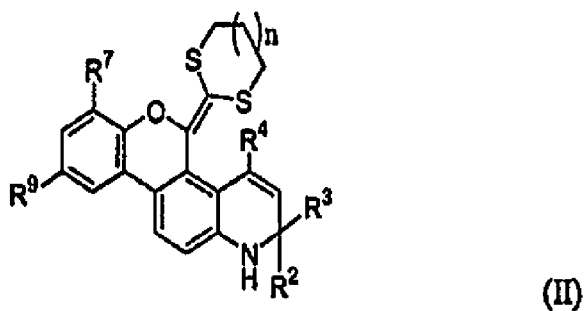

(II)

wherein:
$R^2$ and $R^3$ are $CH_3$;
$R^4$ is selected from the group of F, Cl, Br, $CH_3$, and $CF_3$;
$R^5$ is selected from the group of hydrogen, $C_1$–$C_4$ alkyl, $C_1$–$C_4$ heteroalkyl, and $C_1$–$C_4$ haloalkyl;
$R^7$ is hydrogen or F;
$R^9$ is selected from the group of hydrogen, F, Cl, Br, CN, $OCH_3$, $CH_3$, and $CF_3$;
n is 0, 1, 2 or 3;
or a pharmaceutically acceptable salt thereof.

Col. 20-21 line 49–19  
8. A pharmaceutical composition comprising a pharmaceutically acceptable carrier and a compound of formula:

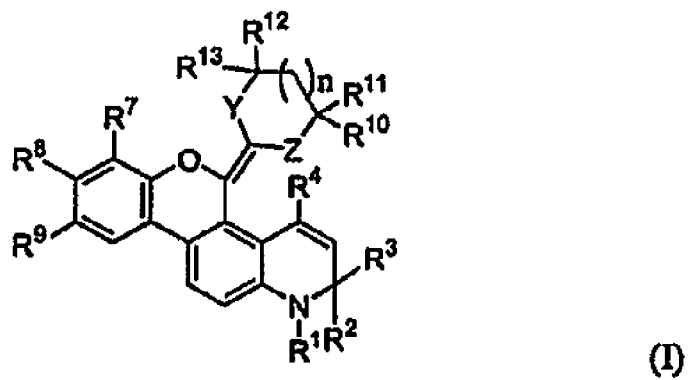

(I)

UNITED STATES PATENT AND TRADEMARK OFFICE
CERTIFICATE OF CORRECTION

PATENT NO. : 7,084,151 B2
APPLICATION NO. : 10/684227
DATED : August 1, 2006
INVENTOR(S) : Lin Zhi et al.

It is certified that error appears in the above-identified patent and that said Letters Patent is hereby corrected as shown below:

wherein:
  $R^1$ is selected from the group of hydrogen, $C_1$–$C_4$ alkyl, $COR^5$, $CO_2R^5$, and $SO_2R^5$;
  $R^2$ and $R^3$ each independently is selected from the group of $C_1$–$C_4$ alkyl;
  $R^4$ is selected from the group of hydrogen, F, Cl, Br, $C_1$–$C_4$ alkyl, and $C_1$–$C_4$ haloalkyl;
  $R^5$ and $R^6$ each is independently selected from the group of hydrogen, and $C_1$–$C_4$ alkyl;
  $R^7$ through $R^9$ each independently is selected from the group of hydrogen, F, Cl, Br, CN, $OR^5$, $C_1$–$C_8$ alkyl, $C_1$-$C_8$ heteroalkyl, and $C_1$–$C_8$ haloalkyl;
  $R^{10}$ through $R^{15}$ each independently is selected from the group of hydrogen, F, Cl, $OR^5$ $C_1$–$C_4$ alkyl, $C_1$–$C_4$ haloalkyl; or
  $R^{12}$ and $R^{14}$ taken together form a bond, when Y is $CR^{14}R^{15}$; or
  $R^{10}$ and $R^{14}$ taken together form a bond, when Z is $CR^{14}R^{15}$;
  Y and Z each independently is selected from the group of S, and $CR^{14}R^{15}$; and
  n is 0, 1, or 2;
or a pharmaceutically acceptable salt thereof.

Col. 20, Line 21–13
9.  A pharmaceutical composition according to claim 8, wherein:
  $R^1$ is hydrogen;
  $R^2$ and $R^3$ is $CH_3$;
  $R^4$ is selected from the group of F, Cl, Br, $CH_3$ and $CF_3$;
  $R^7$ is hydrogen or F;
  $R^8$ is selected from the group of H, $CH_3$, OH, and $OCH_3$;
  $R^9$ is selected from the group of hydrogen, F, Cl, Br, CN, $OCH_3$, $CH_3$, and $CF_3$;
  $R^{10}$, $R^{11}$, $R^{13}$, $R^{15}$ each independently is selected from the group of hydrogen, F, Cl, $CH_3$, and $CF_3$; and

UNITED STATES PATENT AND TRADEMARK OFFICE
CERTIFICATE OF CORRECTION

PATENT NO.       : 7,084,151 B2
APPLICATION NO.  : 10/684227
DATED            : August 1, 2006
INVENTOR(S)      : Lin Zhi et al.

It is certified that error appears in the above-identified patent and that said Letters Patent is hereby corrected as shown below:

$R^{12}$ and $R^{14}$ taken together form a bond, when Y is $CR^{14}R^{15}$.

Signed and Sealed this

Sixteenth Day of January, 2007

JON W. DUDAS
*Director of the United States Patent and Trademark Office*